June 22, 1943. P. B. HOFFMAN Plant Pat. 593

PEACH TREE

Filed Dec. 28, 1942

INVENTOR
P. B. Hoffman
BY
Webster & Webster
ATTORNEYS

Patented June 22, 1943

Plant Pat. 593

UNITED STATES PATENT OFFICE

593

PEACH TREE

Philip B. Hoffman, Marysville, Calif.

Application December 28, 1942, Serial No. 470,365

1 Claim. (Cl. 47—62)

The present discovery relates to a new and distinct variety of peach tree; the variety being a clingstone and especially suitable for canning use.

This new and distinct variety of peach tree somewhat resembles the Phillips cling, particularly as to the ripening period of the fruit, but is otherwise readily distinguishable therefrom; the instant variety being characterized by its glandless leaves, high productivity, lack of defects and gum, the fine texture of the flesh of the fruit, the excellent color of the fruit after canning, and the flavor of the fruit when canned which closely resembles the desirable flavor of canned freestone variety peaches.

The present variety of clingstone peach was discovered by me growing as a chance seedling on my ranch at Live Oak, California. The parent tree is approximately nine years old and first fruited in 1935. Subsequently the variety has been asexually propagated by budding and grafting; the trees of the new variety thus reproduced now being in bearing and have been found to maintain in full the unique characteristics of the original tree and its fruit.

Figure 1:
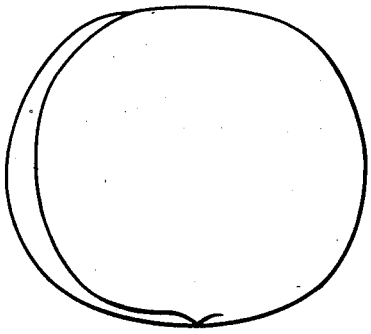
Figure 1 is an outline showing generally the configuration of the fruit.
Figure 2:
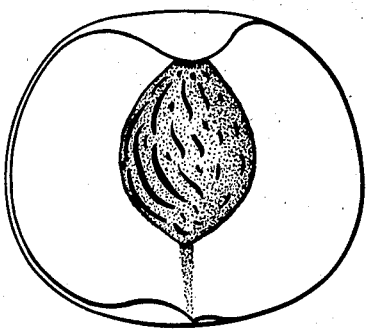
Figure 2 is a sectional view taken axially of the fruit with the stone exposed.
Figure 3:
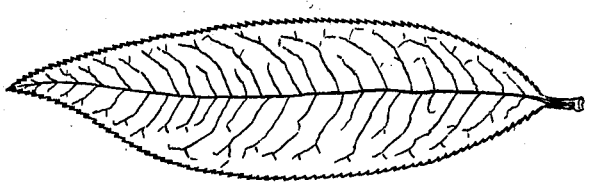
Figure 3 is an elevation of one of the leaves.

Referring now in detail to the new and distinct variety of peach, the following is a detailed description of the tree and its fruit:

*Tree*

The tree is of medium size, of vigorous growth, upright, hardy, very productive and a regular bearer. The trunk is stocky and the branches are of medium size with smooth brown bark which is rather dull. The lenticels are small.

*Leaves*

The leaves of the variety average 3½″ in length and 1$\frac{3}{16}$″ in width; being of medium size, obovate, lanceolate, and acutely pointed. The leaves are thin, dark green in color, and smooth. The margin is finely serrate, while the petiole is of medium length and thickness.

The leaves are glandless; this being one of the unique characteristics of the variety, and by means of which it may be distinguished from many other varieties of clingstone peaches, such as the Phillips cling.

*Flowers*

The flowers begin to bloom on or about March 10 and are in full bloom approximately five days later. The blooming date is thus medium as compared with other varieties, and the flowers are of medium size, and salmon in color.

*Fruit*

The fruit is of a uniform medium size; the average diameter axially being 3½″, and 3¼″ transversely in the suture plane. In shape, the fruit is uniform, symmetrical and globose. The suture is medium shallow, deepening at the apex, discontinuous at apex, and has a slight depression beyond the pistil point. The ventral surface is rounded strongly, lipped toward the apex and slightly toward the base, and the lips are unequal. The cavity is rounded and elongated in the suture plane with the suture showing on one side. The cavity averages ⅝″ in depth and ¾″ in breadth. The base is rounded, the apex short, and the pistil point apical.

The skin of the fruit is thin and tender, being tenacious to the flesh. There is substantially no tendency of the skin to crack, and its color is deep yellow overspread with a light blush. Down is short and abundant.

The flesh of the fruit is yellow, while the surface of the pit cavity is pink. The juice of the fruit is moderate and its texture is firm, fine and crisp. The fibers are few, fine and tender, and the fruit ripens quite evenly. The flavor is mild and the aroma pronounced.

The approximate dates of first and last picking in Sutter County, California, are September 9 and September 20, respectively.

*Stone*

The stone is a cling and adheres to the flesh over the entire surface along both dorsal and ventral edges. The fibers are short. The stone is of relatively small size, averaging 1⅜″ in length, 1⅛″ in breadth and ⅞″ in width. The stone is obovoid, cuneate toward base. The base is straight, the hilum broad, the apex rounded, the sides unequal, and the surface regular, ridged near the base and pitted throughout. The ridges are rounded; the pits elongated; and the ventral edge is thick with a slight wing. The dorsal edge is full with a shallow groove toward the base. The ridges are interrupted. The stone is reddish yellow in color and has slight tendency to split.

Careful observation since discovery of the variety discloses that the variety has excellent keeping as well as shipping qualities, and has good resistance to insects and plant diseases.

As compared to the Phillips cling, the present variety has approximately the same ripening period and both are marketable at substantially the same time. However, the herein described variety of peach is characterized, and distinguished from the Phillips cling, by its glandless leaves, together with high productivity, lack of defects and gum, the fine texture of the flesh of the fruit, and the excellent color of the flesh of the fruit after canning. In addition, the fruit when canned has a flavor similar to the tasty flavor of canned freestone variety peaches. However, the instant peach being a cling with firm flesh avoids the problems encountered in the canning of soft-fleshed freestone varieties.

The tree and its fruit as herein described may vary in slight details due to climatic and soil conditions under which the variety may be grown.

Having thus described my discovery I claim:

A new and distinct variety of peach tree characterized by glandless leaves, high productivity, lack of defects and gum, and clingstone fruit ripening at approximately the same time as the Phillips cling and having flesh of fine texture, excellent color after canning, and a flavor when canned resembling canned freestone variety peaches.

PHILIP B. HOFFMAN.